US012648795B2

(12) United States Patent
Sackett

(10) Patent No.: US 12,648,795 B2
(45) Date of Patent: Jun. 9, 2026

(54) SAFETY TROCAR ASSEMBLY

(71) Applicant: Samuel Gregory Sackett, Dublin, OH (US)

(72) Inventor: Samuel Gregory Sackett, Dublin, OH (US)

( * ) Notice: Subject to any disclaimer, the term of this patent is extended or adjusted under 35 U.S.C. 154(b) by 1052 days.

(21) Appl. No.: 17/752,253

(22) Filed: May 24, 2022

(65) Prior Publication Data

US 2022/0378475 A1     Dec. 1, 2022

Related U.S. Application Data

(60) Provisional application No. 63/192,894, filed on May 25, 2021.

(51) Int. Cl.
A61B 17/34          (2006.01)

(52) U.S. Cl.
CPC ...... A61B 17/3496 (2013.01); A61B 17/3421 (2013.01)

(58) Field of Classification Search
CPC ............ A61B 17/3496; A61B 17/3421; A61B 2017/00548; A61B 2090/034; A61B 17/3415
See application file for complete search history.

(56) References Cited

U.S. PATENT DOCUMENTS

| | | |
|---|---|---|
| 5,275,583 A | 1/1994 | Crainich |
| 5,295,977 A | 3/1994 | Cohen et al. |
| 5,607,405 A | 3/1997 | Decker et al. |

(Continued)

FOREIGN PATENT DOCUMENTS

| | | |
|---|---|---|
| CA | 1 326 424 C | 1/1994 |
| CA | 1 336 563 C | 8/1995 |

(Continued)

OTHER PUBLICATIONS

Notification of Transmittal of the International Search Report and the Written Opinion of the International Searching Authority, or the Declaration dated Sep. 8, 2022 for International Patent Application No. PCT/US2022/030711 (9 pages).

(Continued)

*Primary Examiner* — Chelsea E Stinson
*Assistant Examiner* — Nelson Louis Alvarado, Jr.
(74) *Attorney, Agent, or Firm* — TAYLOR & EDELSTEIN, PC

(57)          ABSTRACT

A trocar assembly includes a deployment assembly including: a cannula having an open end; a trocar disposed in the cannula and having a spear end; and an energizer acting on the trocar and configured to force the trocar from a safety position where the spear end is entirely within the cannula to an extended position where the spear end extends out of the open end; a key releasably coupled with the trocar and extending through the cannula such that the key holds the trocar in the safety position when coupled with the trocar in the safety position and uncoupling the key from the trocar allows the energizer to force the trocar from the safety position to the extended position; and a sheath assembly removably coupled to the deployment assembly, the sheath assembly including a sheath that covers the open end of the cannula.

21 Claims, 15 Drawing Sheets

(56) References Cited

U.S. PATENT DOCUMENTS

| | | | |
|---|---|---|---|
| 5,637,096 A | 6/1997 | Yoon | |
| 5,674,237 A | 10/1997 | Ott | |
| 5,772,678 A | 6/1998 | Thomason et al. | |
| 5,868,773 A | 2/1999 | Danks et al. | |
| 5,984,941 A | 11/1999 | Wilson et al. | |
| 6,613,039 B1 | 9/2003 | Namba | |
| 6,626,868 B1 | 9/2003 | Prestidge et al. | |
| 7,731,730 B2 | 6/2010 | Popov | |
| 7,909,802 B2 | 3/2011 | Sauter et al. | |
| 7,938,810 B2 | 5/2011 | Spranza et al. | |
| 8,409,232 B2 | 4/2013 | Muto et al. | |
| 8,911,463 B2 | 12/2014 | Fischvogt | |
| 9,113,953 B2 | 8/2015 | Smith | |
| 10,980,522 B2 | 4/2021 | Muse | |
| 12,279,793 B2 | 4/2025 | Amon | |
| 2001/0029387 A1* | 10/2001 | Wolf | A61B 17/3496 |
| | | | 606/167 |
| 2009/0204140 A1* | 8/2009 | Dandl | A61B 17/3417 |
| | | | 606/185 |
| 2011/0118673 A1 | 5/2011 | Dringenberg | |
| 2013/0217974 A1* | 8/2013 | Levy | A61B 17/3421 |
| | | | 600/210 |
| 2013/0338577 A1 | 12/2013 | Al-Habaibeh et al. | |
| 2015/0258294 A1 | 9/2015 | Nhan et al. | |
| 2019/0374746 A1 | 12/2019 | Konh | |

FOREIGN PATENT DOCUMENTS

| | | |
|---|---|---|
| CA | 2 144 428 | 8/1999 |
| CA | 2 156 786 C | 5/2007 |

OTHER PUBLICATIONS

Extended European Search Report dated Feb. 26, 2025 for European Patent Application No. 22811973.1 (9 pages).

* cited by examiner

SAFETY TROCAR ASSEMBLY

CROSS REFERENCE TO RELATED APPLICATIONS

This is a non-provisional application based upon U.S. provisional patent application Ser. No. 63/192,894, entitled "SAFETY TROCAR ASSEMBLY", filed May 25, 2021, which is incorporated herein by reference.

BACKGROUND OF THE INVENTION

1. Field of the Invention

The present invention relates to surgical devices, and, more particularly, to trocar assemblies.

2. Description of the Related Art

Trocars are frequently used in medical procedures to form an opening in a patient's soft tissue and skin. To form the opening, the trocar must have a sharpened spear end that pierces the patient's soft tissue and skin to form an opening. Handling the trocar before piercing the patient's skin can represent a sharps sticking hazard to medical professionals. A medical professional may inadvertently pierce their own skin with the spear end of the trocar when unpackaging a trocar and passing the trocar to a surgeon. If a trocar becomes contaminated before use, it must be disposed of and a second trocar is required for the procedure.

When the trocar is used to form an opening, for example, to insert a wound drain into a surgical site, it may be hazardous for a surgeon. Piercing the patient's skin with the trocar requires moving the trocar with considerable speed and force from the inside of a body cavity, through soft tissue and skin, until the trocar exits the body. A surgeon's glove is often covered with synovial fluid, making the glove and trocar slippery when attempting to force the trocar through the soft tissue and skin. Once a trocar passes through soft tissue, it may be difficult and hazardous to grasp, remove and discard. Further, it is usually the spear end of the trocar that extends out of the skin after forming the opening, which presents a significant sticking hazard and blood borne pathogen risk to medical professionals.

What is needed in the art is a way to unpackage, pass, insert, remove and dispose of a trocar during a medical procedure that reduces the risk of inadvertent sticks, contamination risks to patients and blood borne pathogen risks to medical staff by the spear end of the trocar.

SUMMARY OF THE INVENTION

The present invention provides a trocar assembly with a key that holds a trocar in a safety position so a spear end of the trocar is held within a cannula until the key is uncoupled from the trocar to allow an energizer to force the trocar to an extended position where the trocar extends out of an open end of the cannula. A removable sheath covers the open end of the cannula and may fully or partially cover the trocar in the extended position.

The invention in one form is directed to a trocar assembly including: a deployment assembly including: a trocar extension assembly including: a cannula having an open end; a trocar disposed in the cannula and having a spear end; and an energizer acting on the trocar and configured to force the trocar from a safety position where the spear end is entirely within the cannula to an extended position where the spear end extends out of the open end of the cannula; a locking assembly including a key releasably coupled with the trocar and extending through the cannula such that the key holds the trocar in the safety position when coupled with the trocar in the safety position and uncoupling the key from the trocar allows the energizer to force the trocar from the safety position to the extended position; and a sheath assembly removably coupled to the deployment assembly, the sheath assembly including a sheath that covers the open end of the cannula.

The invention in another form is directed to a method of inserting and removing a trocar, the trocar being disposed within a cannula. The method includes: energizing an energizer that acts on the trocar, the energizer being configured to force the trocar from a safety position where a spear end of the trocar is entirely within the cannula and an extended position where the spear end extends out of an open end of the cannula, a coupled sheath covers the open end of the cannula; holding the trocar in the safety position with a key that is coupled with the trocar and extends through the cannula; uncoupling the sheath so the open end of the cannula is uncovered; placing the open end of the cannula on or adjacent to the skin of a patient; moving the key to release the trocar so the energizer forces the trocar from the safety position to the extended position such that the spear end pierces the skin of the patient; and capturing the spear end of the trocar using the sheath by fitting an extension post of the sheath in an extraction opening formed in the trocar.

An advantage of the present invention is the spear end of the trocar can be held within the cannula while unpackaging, passing, and positioning the trocar within a surgical site until the key is removed, reducing the risk that the spear end will inadvertently harm medical staff.

Another advantage is the removable sheath covers the spear end in the extended position to protect users even if the spear end is inadvertently deployed.

Yet another advantage is the sheath can be used to capture and conceal the spear end during removal and disposal of the trocar after deployment, further reducing the risk of medical personnel sticking themselves with the spear end of the trocar.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figures 1, 2:
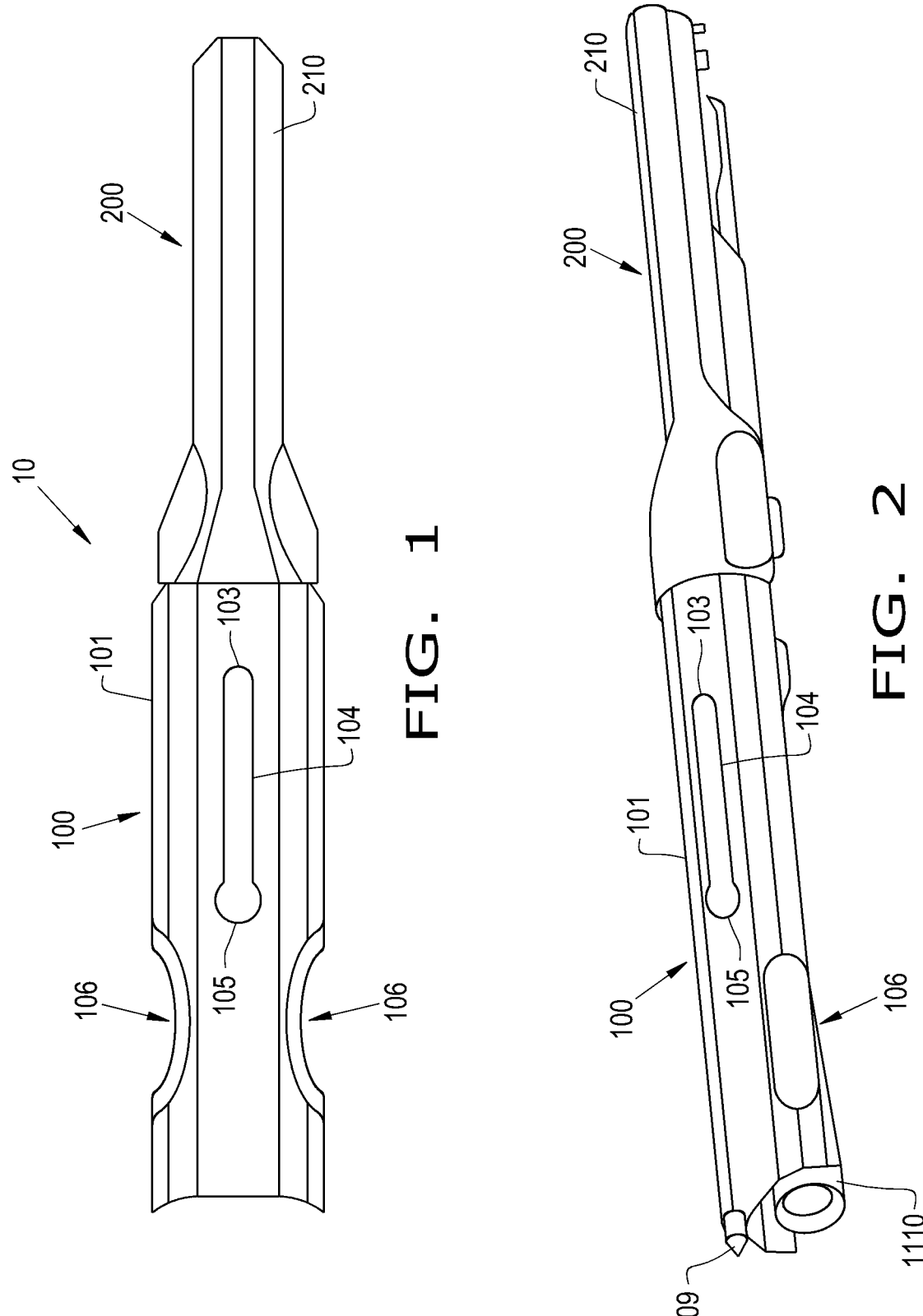
FIG. 1 is a top view of an exemplary embodiment of a trocar assembly provided according to the present invention that includes a deployment assembly and a sheath assembly removably coupled to the deployment assembly.
FIG. 2 is a perspective view of the trocar assembly of FIG. 1.
Figure 3:
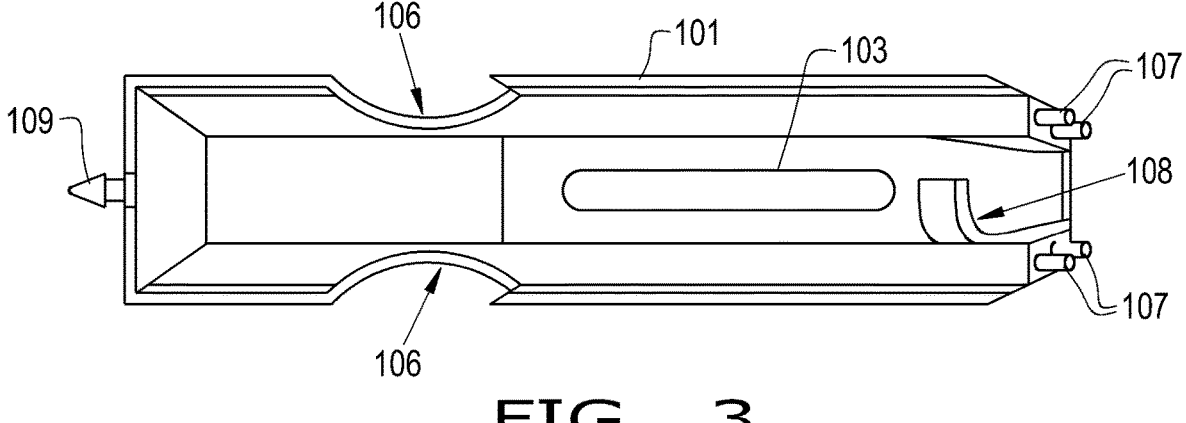
FIG. 3 is a perspective view of a portion of a housing of the trocar assembly of FIGS. 1-2.

Referring now to the drawings, and more particularly to FIGS. 1-2, there is shown an exemplary embodiment of a trocar assembly 10 which generally includes a deployment assembly 100 and a sheath assembly 200 that is removably coupled to the deployment assembly 100. In this respect, the sheath assembly 200 can be uncoupled from the deployment assembly 100, as will be described further herein. The trocar assembly 10 is configured to be used in conjunction with a drain device in order to drain fluid from a surgical site. The trocar assembly 10 can thus be adjusted to couple with a variety of different drain devices in order to drain fluid.

The deployment assembly 100, which is illustrated separately from the sheath assembly 200 in FIGS. 3-11D, generally includes a housing 101 in which a trocar extension assembly 110 (illustrated separately in FIGS. 10-11D) is disposed and a hose barb 1130 configured to couple a cannula 1110 to a hose outflow tube. The housing 101 also houses a locking assembly 600 (illustrated separately in FIGS. 6-8) that is configured to activate the trocar extension assembly 110, as will be described further herein. In some embodiments, the deployment assembly 100 also includes a hose clamp 900 (illustrated separately in FIG. 9) that is configured to clamp on a hose outflow tube and further secure the hose outflow tube to the cannula 1110.

The housing 101 has a track 103 formed therein that is shaped and sized to accept a key 700 (illustrated in FIGS. 7-8) that is used to activate the trocar extension assembly 110. The track 103 may be an elongated slot with a first section 104 defining a first width and a second section 105 defining a second width that is larger than the first width. As illustrated, the second section 105 may be located closer to a rear end of the trocar extension assembly 110, i.e., closer to the hose clamp 900 and the hose barb 1130. The housing 101 may also have one or more grip sections 106 formed therein, illustrated as arced cutouts, that are shaped and sized for a user to grip during use of the trocar assembly 10. The grip sections 106 may be textured, as illustrated, to further improve gripping of the trocar assembly 10. In some embodiments, the grip sections 106 include a soft grip material, such as medical grade silicone, that further improves the ergonomics of the trocar assembly 10. To removably couple the deployment assembly 100 and the trocar extension assembly 110 to the sheath assembly 200, one or more assembly posts 107, illustrated as four assembly posts, may be disposed on a front of the housing 101 and shaped to be placed in respective assembly openings 211 formed in a sheath 210 of the sheath assembly 200 and form a press fit, coupling the assemblies 100, 200 together. The housing 101 may also include a cannula support 108 in which the cannula 1110 is disposed to keep the cannula 1110 in place during use. It should be appreciated that the housing 101 can be formed with a wide variety of shapes and sizes, depending on the configuration of the housed components, and thus the illustrated and described housing 101 is exemplary only.

Figure 4:
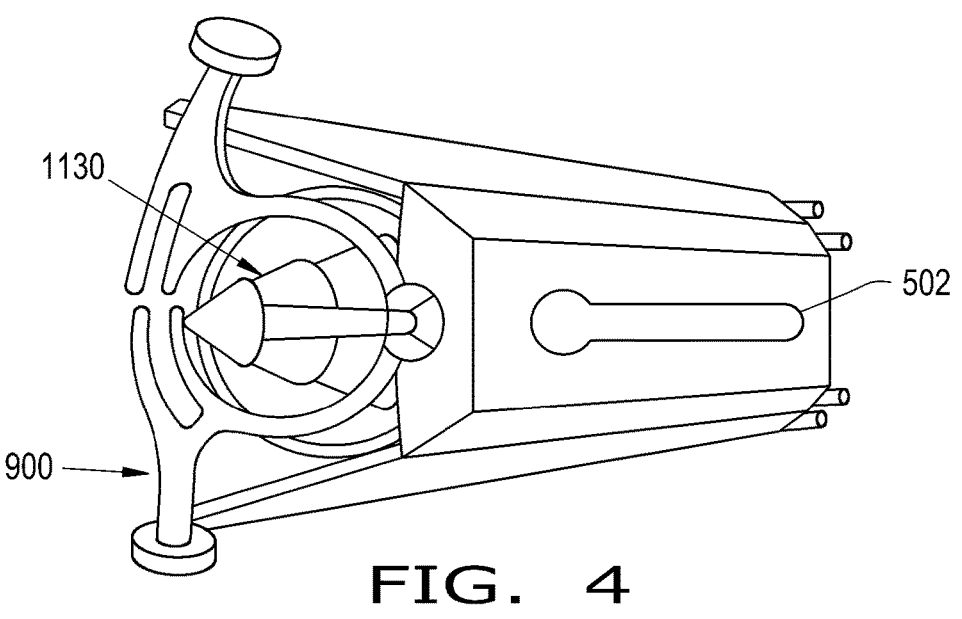
FIG. 4 is a perspective view of a hose clamp and a hose barb of the trocar assembly of FIGS. 1-2.

As specifically illustrated in FIG. 4, the hose clamp 900 and the hose barb 1130 may be disposed on the rear side of the housing 101 to couple with a hose outflow tube. In this respect, the rear side of the housing 101 may represent a coupling end of the housing 101 where the hose outflow tube can couple with the cannula 1110. In some embodiments, the hose barb 1130 and/or the hose clamp 900 may be partially or fully disposed outside of the housing 101 when coupled to the hose outflow tube. The hose clamp 900 may, for example, include a mounting opening 901 that is mounted on a clamp post 109 that extends from the housing 101 to mount the hose clamp 900 to the clamp post 109.

Figure 5:
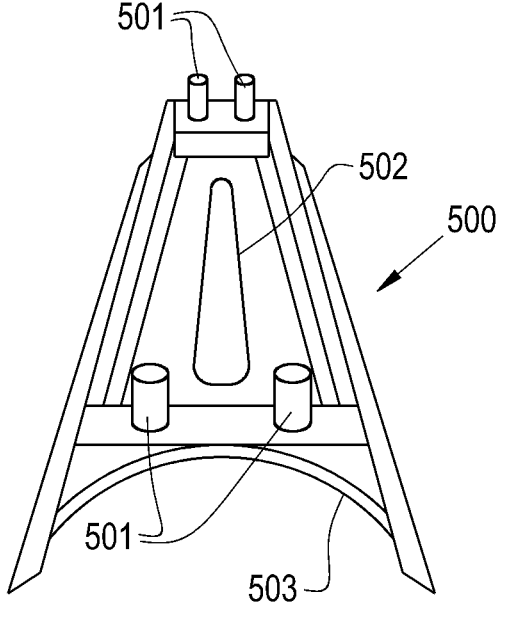
FIG. 5 is a perspective view of an insert of the trocar assembly of FIGS. 1-2.

Referring now to FIG. 5, an insert 500 that may be disposed inside the housing 101 is illustrated. The insert 500 may include the four assembly posts 501 and have an insert key hole track 502 formed therein that is sized and shaped to accept the key 700 and allow movement of the key 700 therein. The insert 500 may have a curved edge 503 that is sized to accommodate the cannula 1110. The insert may also include a plurality of insert teeth 504 that intermesh with corresponding gear teeth 601 of a gear 600, which is illustrated in FIG. 6.

Figure 6:
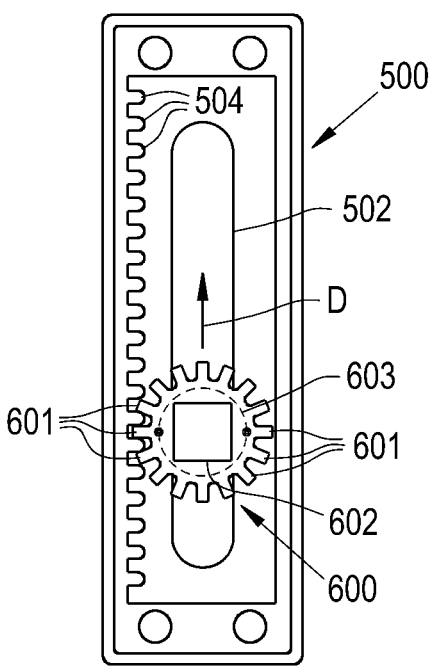
FIG. 6 is a bottom view of a gear engaged with insert teeth of the insert of FIG. 5.

Referring now to FIG. 6, the gear 600 is illustrated with gear teeth 601 intermeshed with the insert teeth 504 of the insert 500, which form a rack. The gear 600 includes a gear opening 602 that is sized and shaped to accept a corresponding section 701 of the key 700 so the key 700 resides partially in the gear opening 602 during use, as will be described further herein. The gear 600 can be locked in a position by a locking system. The locking system may include, for example, a disc 603 (illustrated in dashed lines in FIG. 6) that is carried by the gear 600 and displaces into the second section 105 of the elongated slot of the track 103 when the disc 603 aligns with the second section 105, e.g., by falling into the second section 105 or being pushed into the second section 105 by a spring or other element. When the disc 603 falls into the second section 105 of the elongated slot of the track 103, the gear 600 may be prevented from displacing further. The locking system may alternatively, or in addition, include a pawl, or a series of pawls, to act as a rotation lock so rotation of the gear 600 is restricted to one direction, limiting displacement of the gear 600 to a single linear displacement direction D along the rack after engaging the pawl(s). When the key 700 is inserted in the gear 600, as illustrated in an exploded view in FIG. 8, the key 700 can be rotated to displace the gear 600 along the rack in the displacement direction D, with the locking system preventing the gear 600 from displacing in the opposite direction to the displacement direction D.

Figure 7:
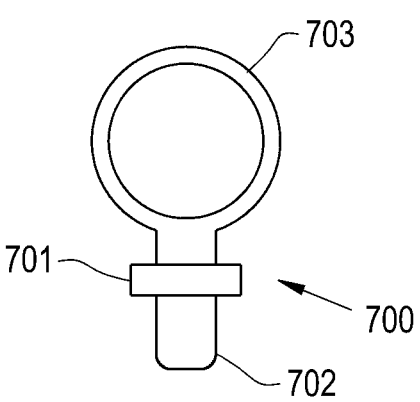
FIG. 7 is a side view of a key that may be used in the trocar assembly of FIGS. 1-2.
Figure 8:
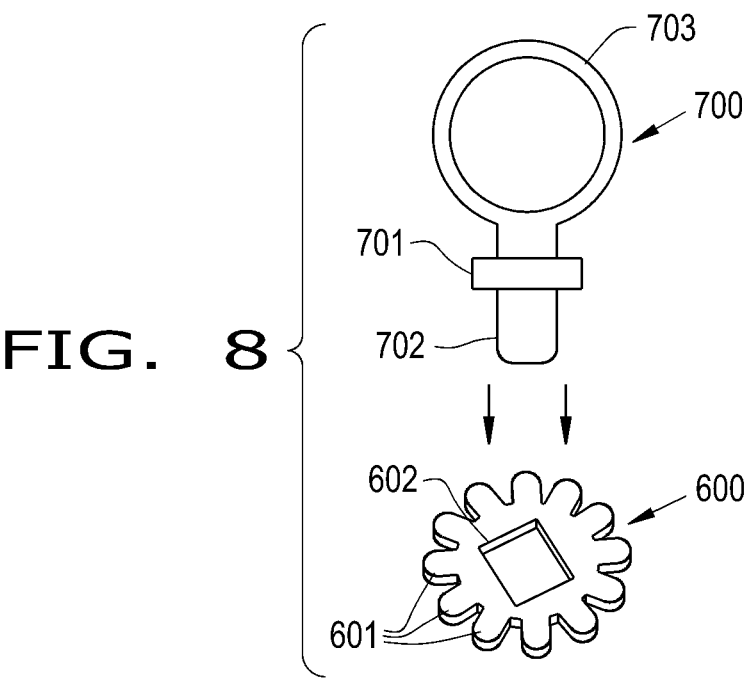
FIG. 8 is an exploded view of the key of FIG. 7 and the gear of FIG. 6.
Figure 9:
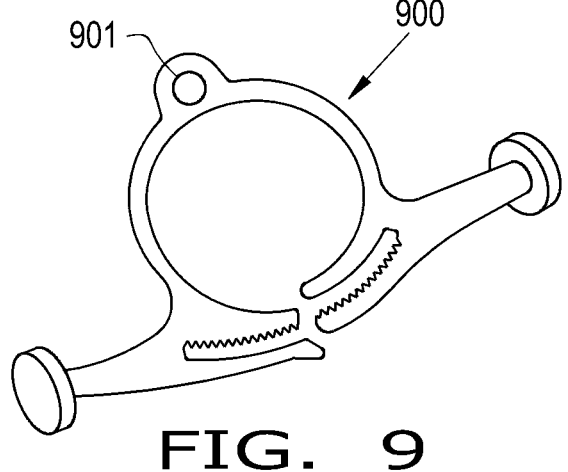
FIG. 9 is a perspective view of a hose clamp that may be included in the trocar assembly of FIGS. 1-2.

The key 700, which is illustrated alone in FIG. 7, includes a gear engaging section 701 that, in the illustrated embodiment, has a square shape to fit within the gear opening 602 of the gear 600, which is also square. The square shape of the gear engaging section 701 of the key 700 and the corresponding gear opening 602 in the gear 600 promotes rotational stability, but it should be appreciated that the shape of the gear engaging section 701 and the gear opening 602 can be configured differently. The gear engaging section 701 may define a width that is greater than the first width of the track 103 of the housing 101 but smaller than the second width of the track 103, so the key 700 can only be pulled out from the track 103 when the key 700 is disposed in the section 105 of the track 103 with the second width. In addition to the gear engaging section 701, the key 700 has a trocar engaging section 702 on one side of the gear engaging section 701 and a pull ring 703 on an opposite side of the gear engaging section 701.

Figures 10, 11A, 11B, 11C, 11D:
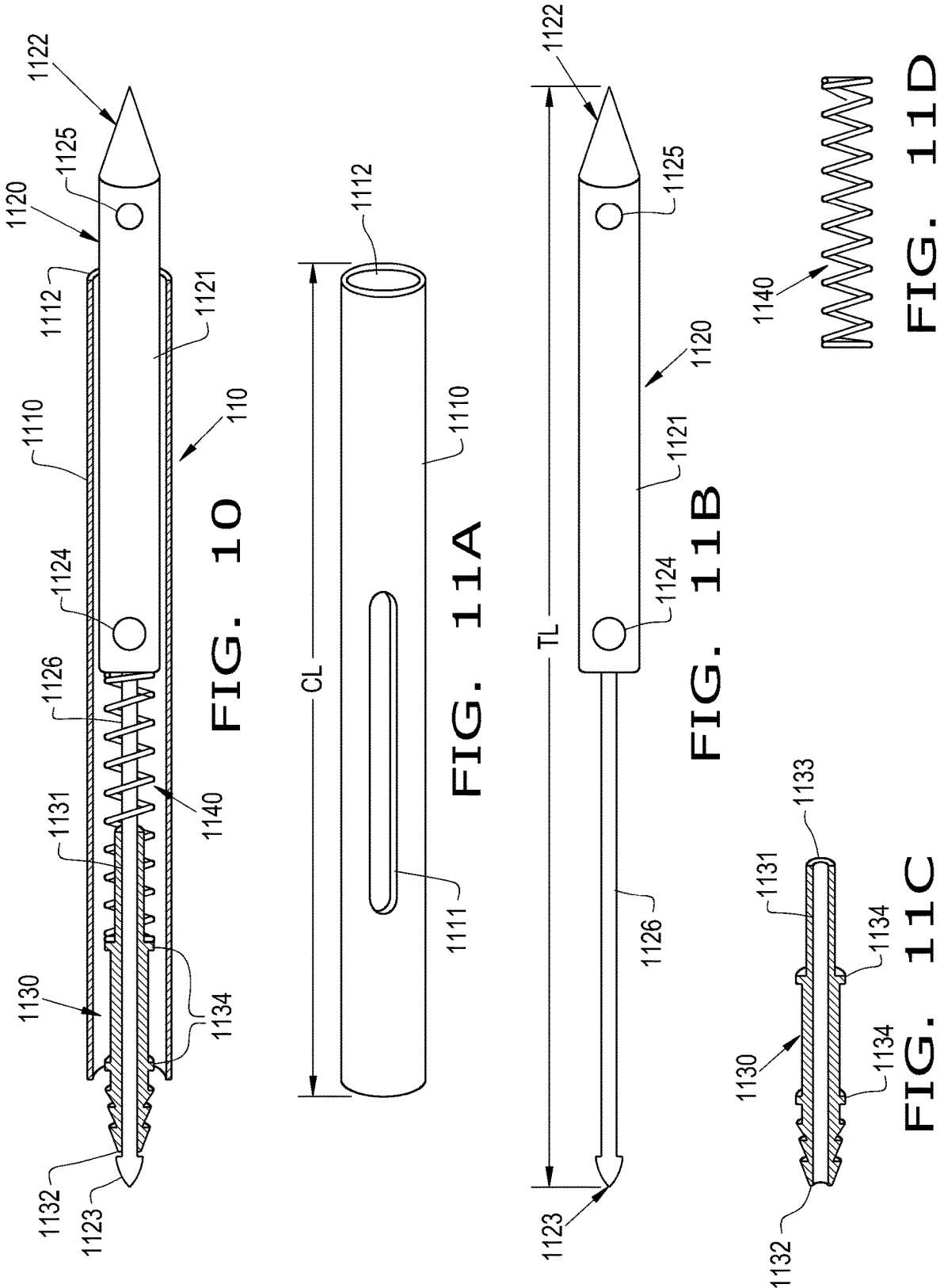
FIG. 10 is a cross-sectional view of a trocar extension assembly of the trocar assembly of FIGS. 1-2 with a trocar in an extended position.
FIG. 11A is a top view of a cannula of the trocar extension assembly of FIG. 10.
FIG. 11B is a top view of the trocar of the trocar extension assembly of FIG. 10.
FIG. 11C is a cross-sectional view of a hose barb of the trocar extension assembly of FIG. 10.
FIG. 11D is a side view of a spring of the trocar extension assembly of FIG. 10.

Referring now to FIGS. 10-11D, an exemplary embodiment of a trocar extension assembly 110 provided according to the present invention is illustrated, with the trocar extension assembly 110 illustrated in an assembled state in FIG. 10 and the constituent components 1110, 1120, 1130, 1140 of the trocar extension assembly 110 illustrated in FIGS. 11A, 11B, 11C, and 11D. The trocar extension assembly 110 includes: the cannula 1110, which is illustrated alone in FIG. 11A; a trocar 1120, which may also be commonly referred to as an "awl" and is illustrated alone in FIG. 11B; the hose barb 1130, which is illustrated alone in FIG. 11C; and an energizer 1140 in the form of a spring, which is illustrated alone in FIG. 11D. The cannula 1110 may be a cylindrical tube, which can comprise stainless steel or any other suitable material, that includes a cannula track 1111 in which the trocar engaging section 702 of the key 700 is disposed. The trocar engaging section 702 of the key 700 can be displaced within the cannula track 1111 to allow displacement of the gear 600 and the trocar 1120.

As illustrated in FIG. 11B, the trocar 1120 includes a trocar body 1121, a spear end coupled 1122 to the trocar body 1121, and an anchor 1123 at an end of the trocar 1120 that is opposite the spear end 1122. The trocar 1120 may comprise a polymer, such as a medical grade ultra-high molecular weight polyethylene, but it should be appreciated that the trocar 1120 may be formed of any suitable material(s). The spear end 1122 of the trocar is pointed and sharp in order to pierce the skin of a patient as the trocar 1120 is forced out of the cannula 1110 by the energizer 1140. It should thus be appreciated that the spear end 1122 of the trocar 1120 may be shaped and configured in a variety of ways to provide a piercing element for the trocar 1120. The trocar body 1121 of the trocar 1120 may have at least two openings: a trocar key opening 1124 that is shaped and sized to accept the trocar engaging section 702 of the key 700 to couple the key 700 to the trocar 1120 and an extraction opening 1125 that can be engaged to extract the trocar 1120 from a patient. The trocar key opening 1124 may be formed adjacent to a first end of the trocar body 1121 adjacent to a stem 1126 of the trocar 1120 that couples the anchor 1123 to the trocar body 1121 and the extraction opening 1125 may be formed adjacent to the spear end 1122 of the trocar 1120. In some embodiments, the stem 1126 and the anchor 1123 are formed integrally with one another but are removably coupled to the trocar body 1121 so the stem 1126 and the anchor 1123 can be removed from the trocar body 1121. The stem 1126 may, for example, include threading and be threaded into a threaded opening formed in the trocar body 1121. The trocar 1120 defines a trocar length TL that may be greater than a cannula length CL of the cannula 1110 so a portion of the trocar 1120 always extends out of the cannula 1110. While the trocar 1120 is illustrated as being non-cannulated, it should be appreciated that, in some embodiments, the trocar 1120 is cannulated.

Figure 14:
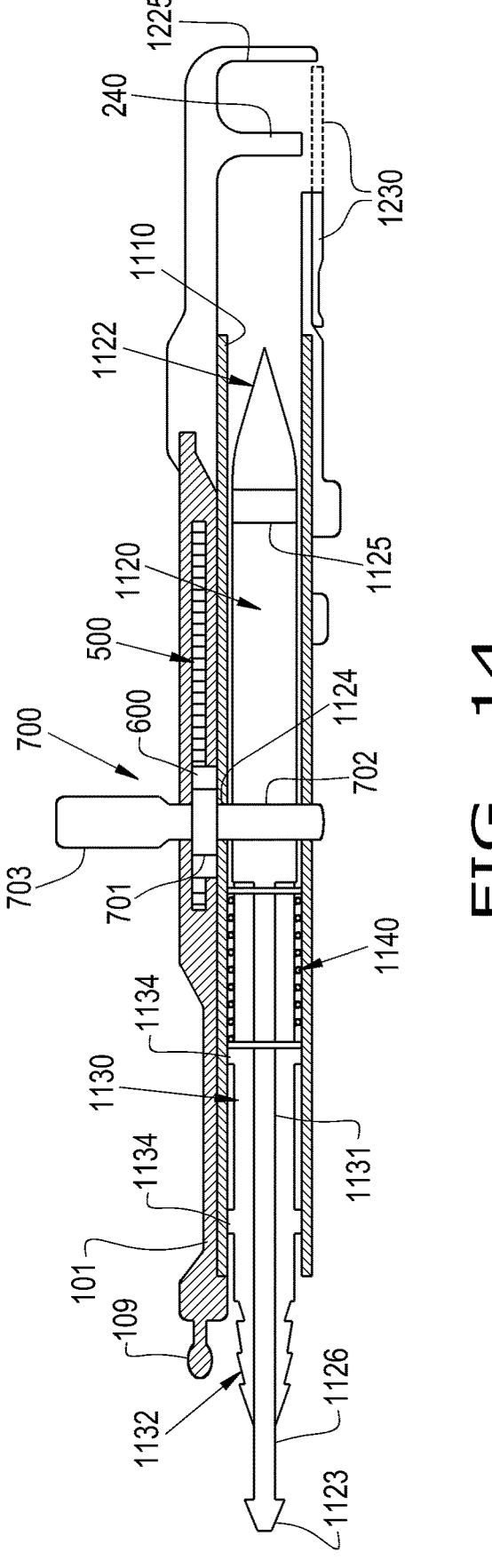
FIG. 14 is a cross-sectional view of the trocar assembly of FIGS. 1-2 when the trocar is in a safety position and held in the safety position by the key.

The stem 1126 of the trocar 1120 may be disposed within a through-opening 1131 formed in the hose barb 1130. The hose barb 1130 is configured to couple to a hose outflow tube. The hose barb 1130 may have a barbed end 1132 and an end 1133, such as a cylindrical end, opposite the barbed end 1132, with the through-opening 1131 extending through the barbed end 1132 and the opposite end 1133. The anchor 1123 of the trocar 1120 may abut against the barbed end 1132 when the trocar 1120 is in an extended position, illustrated in FIG. 10, so the barbed end 1132 can limit the displacement of the trocar 1120 within the cannula 1110. The hose barb 1130 may include one or more bearing sections 1134 that define a greater diameter than the rest of the hose barb 1130. The bearing section(s) 1134 may bear against the cannula 1110 (as best illustrated in FIG. 14) to stabilize the hose barb 1130 within the cannula 1110 so movement of the hose barb 1130 within the cannula 1110 is limited. The bearing section(s) 1134 may fit within one or more corresponding grooves (or other features) formed in the cannula 1110 to further limit possible movement of the hose barb 1134 within the cannula 1110.

An energizer 1140, illustrated by itself as a coil spring in FIG. 11D, acts on the trocar 1120. As illustrated, the energizer 1140 is disposed on the stem 1126 of the trocar 1120 and may bear against one of the bearing sections 1134 of the hose barb and the first end of the trocar body 1121. While the energizer 1140 is illustrated and described herein as a spring, it should be appreciated that the energizer 1140 may take other forms, such as a gas cylinder, according to the present invention. The spring 1140 may be compressed between the bearing section 1134 and the first end by displacement of the trocar 1120 during rotation of the key 700, as illustrated in FIG. 14, which energizes the spring 1140 and moves the trocar 1120 to a safety position where the spear end 1122 is disposed entirely within the cannula 1110. As the trocar 1120 moves to the safety position, the hose barb 1130 may also displace in the same direction to extend out of the housing 101 and engage a hose outflow tube until the barbs and/or bearing section(s) 1134 engage the inner hose, groove, or other feature to stop further displacement of the hose barb 1130 within the cannula 1110; when the hose barb 1130 may no longer displace in the cannula 1110, further displacement of the gear 600 and the trocar 1120 compresses the spring 1140. As the key 700 rotates to displace the gear 600, displacing the trocar 1120 as well, the stem 1126 and the anchor 1123 travel through the through-opening 1131 of the hose barb 1130 so the anchor 1123 no longer abuts against the barbed end 1132 of the hose barb 1130 when the barbs and/or bearing section(s) 1134 of the hose barb 1130 has engaged the inner hose or a feature to stop further displacement of the hose barb 1130. The anchor 1123, which may be tapered, and the barbed end 1132 of the hose barb 1130 can thus travel into a hose outflow tube as the key 700 is rotated. Since the key 700 is locked from rotating and displacing in a direction that would cause the spring 1140 to decompress, by friction between the teeth 601 of the gear 600 and the teeth 504 of the rack and/or by a separate locking mechanism, the spring 1140 remains compressed and energized so long as the trocar engaging section 702 of the key 700 is disposed in the trocar key opening 1124. Thus, the key 700 can be used to energize the spring 600 by rotating the key 700 and, when desired, pulled to uncouple the key 700 from the trocar 1120 so the energizer (spring) 1140 is allowed to decompress and force the trocar 1120 from the safety position to the extended position (illustrated in FIG. 10) where the spear end 1122 extends out of an open end 1112 of the cannula 1110 for piercing tissue and skin.

Figure 12:
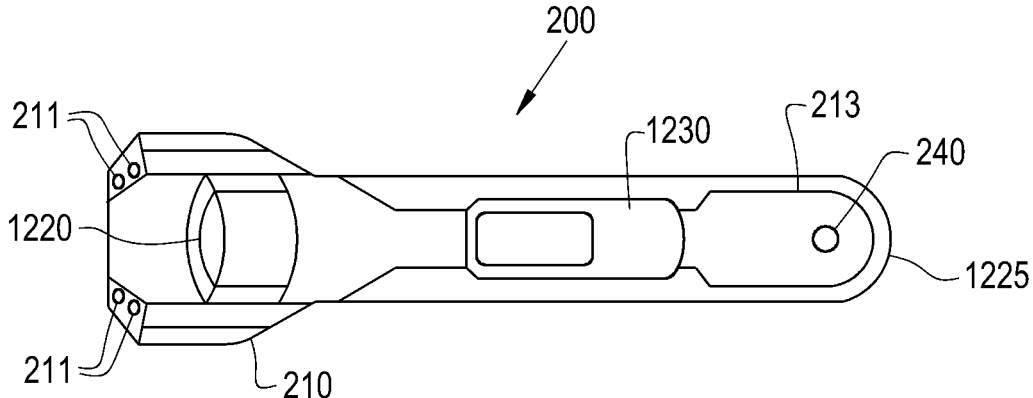
FIG. 12 is a bottom view of the sheath assembly of the trocar assembly of FIG. 1 separated from the deployment assembly.
Figure 13:
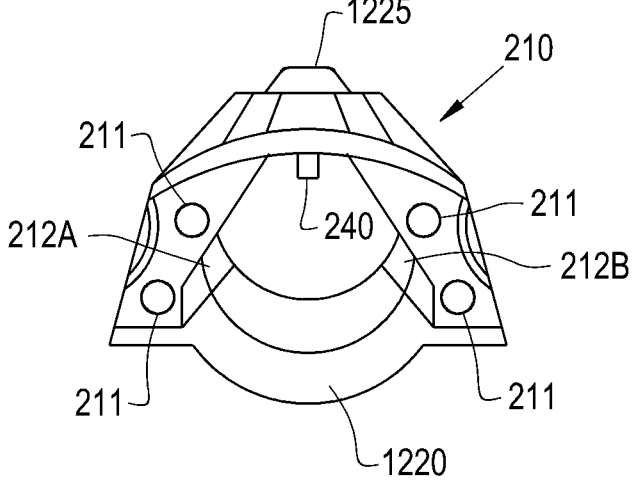
FIG. 13 is a rear view of the sheath assembly of FIG. 12.

Referring now to FIGS. 12-13, the sheath assembly 200 is illustrated separated from the deployment assembly 100. The sheath assembly 200 includes a sheath 210 that removably couples to the housing 101 of the deployment assembly 100. The sheath 210 may include four assembly openings 211 in which the assembly posts 107 of the housing 101 are inserted to couple the sheath 210 to the housing 101. The sheath 210 can be pulled away from the assembly posts 107 to remove the sheath assembly 200 from the deployment assembly 100. The sheath 210 is shaped and sized so that the open end 1112 of the cannula 1110 is covered by the sheath 210 when the sheath assembly 200 is coupled to the deployment assembly 100. In some embodiments, the sheath 210 also covers the spear end 1122 of the trocar 1120 when the trocar 1120 is in the extended position and the sheath assembly 200 is coupled to the deployment assembly 100. In this respect, the sheath assembly 200 prevents the trocar 1120 from inadvertently jabbing a user or person other than the intended patient.

The sheath assembly 200 may include an arced cannula bender 1220 extending between two side walls 212A, 212B of the sheath 210. The cannula bender 1220 may support cannula 1120 and, when desired, be used to bend the cannula 1110 by slightly separating, i.e., partially uncoupling, the sheath assembly 200 from the deployment assembly 100 and pivoting the sheath assembly 200 to cause the desired bending of the cannula 1120. The cannula bender 1220 may be formed of any material and have any shape that is suitable to bend the cannula 1110 as described.

Figure 15:
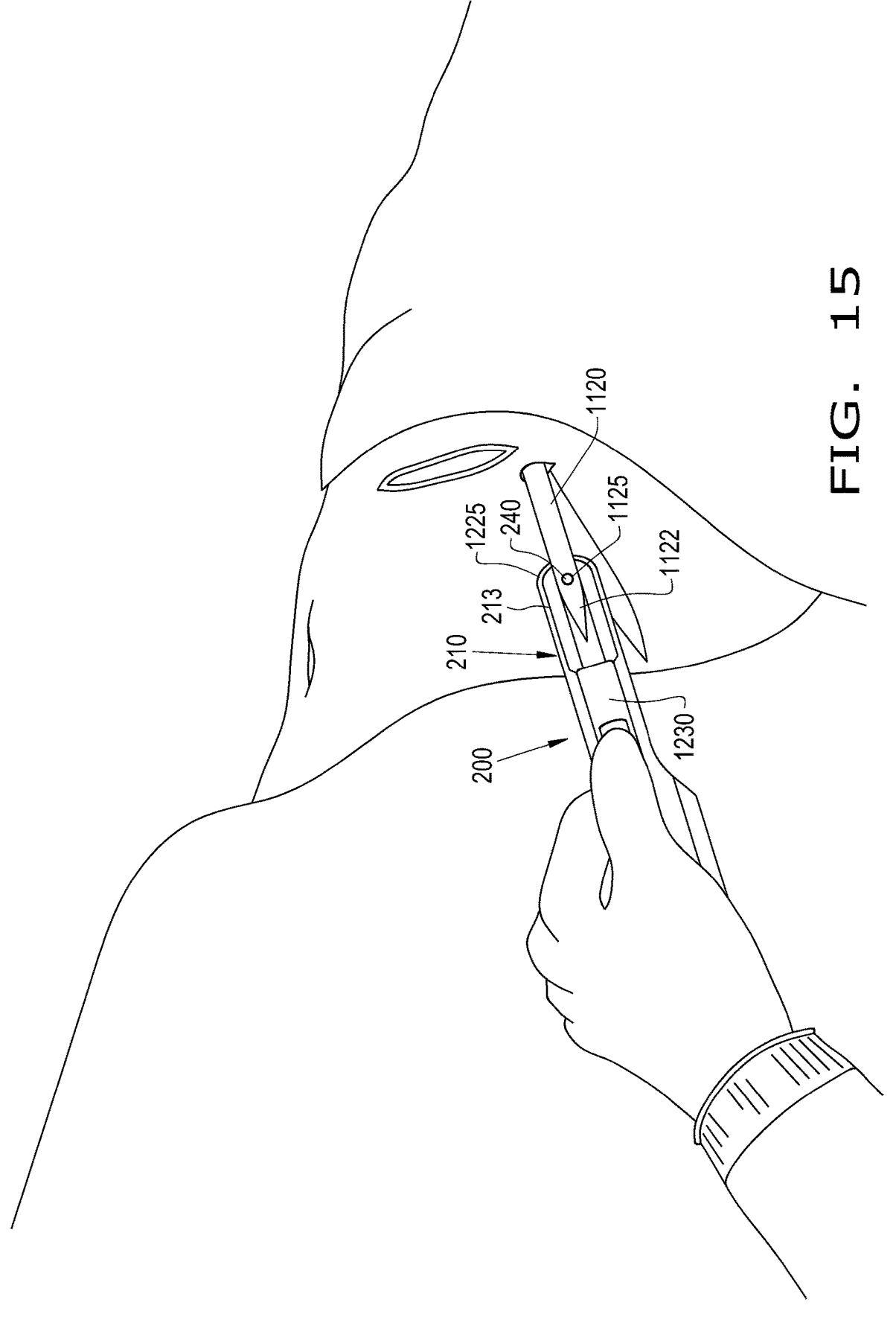
FIG. 15 illustrates the trocar being removed from a patient using the sheath assembly of FIGS. 12-13.

The sheath assembly 200 includes a slidable door 1230 that is slidably coupled to the sheath 210. The slidable door 1230 is slidably coupled to the sheath 210 so the slidable door 1230 can slide between different positions (an open position as illustrated in solid lines and a closed position as illustrated in dashed lines in FIG. 14) to cover or uncover portions of an opening 213 formed in the sheath 210. As illustrated in FIGS. 12-13, as well as FIGS. 14-15, the sheath assembly 200 also includes an extraction post 240 that extends from an interior surface of the sheath 210. The extraction post 240 is shaped and sized to fit within the extraction opening 1125 of the trocar 1120 in order to capture the trocar 1120 and extract the trocar 1120 after deployment of the trocar 1120. When the trocar 1120 extends out of a stab wound, as illustrated in FIG. 15, the extraction post 1224 may be placed in the extraction opening 1125 of the trocar 1120 so the trocar 1120 extends through a through-opening 1225 formed through a front end of the sheath 210 with the spear end 1122 of the trocar 1120 disposed within the sheath 210. When the spear end 1122 is disposed in the sheath 210 and the extraction post 240 of the sheath assembly 200 is disposed in the extraction opening 1125 of the trocar 1120, the slidable door 1230 can be slid to a closed position toward the front end of the sheath 210 to enclose the spear end 1122 of the trocar 1120, which is the sharp part of the trocar 1120, and safely extract the trocar 1120 from the stab wound. The slidable door 1230, when moved to the closed position, can also prevent the extraction post 240 from coming out of the extraction opening 1125, securing the spear end 1122 of the trocar 1120 in the sheath 210. Thus, the sheath assembly 200 can be used to prevent inadvertent jabbing by the spear end 1122 of the trocar 1120 before deployment and also be used to safely extract the trocar 1120 following deployment.

To use the trocar assembly 10, the deployment assembly 100 and the sheath assembly 200 may be initially coupled together. A drain outflow tube may be connected to the trocar 1120 via the hose clamp 900 of the deployment assembly 100. The key 700 is placed so the trocar engaging section 702 is disposed in the trocar key opening 1124 and the gear engaging section 701 is disposed in the gear opening 602. The key 700 is rotated to cause displacement of the gear 600 along the rack, which causes a corresponding displacement of the trocar 1120 and compression of the energizer 1140 (spring). As the key 700 and trocar 1120 displace, the spring 1140 is energized and the anchor 1126 of the trocar 1120 is driven into the drain outflow tube simultaneously. The key 700 is rotated and displaced until the spring 1140 is sufficiently energized to drive the spear end 1122 with enough force to create a stab wound. In some embodiments, the spear end 1122 of the trocar 1120 resides entirely within the cannula 1110, as illustrated in FIG. 14, when the spring 1140 is sufficiently energized. When the spring 1140 is sufficiently energized, the deployment assembly 100 is ready for deployment.

After the deployment assembly 100 is ready for deployment, the sheath assembly 200 may be separated from the deployment assembly 100. If bending of the cannula 1110 is desired, the sheath assembly 200 may be partially uncoupled from the deployment assembly 100 so the cannula bender 1220 remains in contact with the cannula 1110. A user may then press down or up on the sheath assembly 200 to bend the cannula 1110 in the desired fashion. After bending, or if no bending is desired, the sheath assembly 200 may be completely removed from the deployment assembly 100.

With the deployment assembly 100 ready for deployment, the deployment assembly 100 can be placed so the open end 1112 of the cannula 1110 is on or adjacent to the skin so the open end 1112 of the cannula 1110 may be pressed firmly against the underside of the skin where the stab wound is to be created. The key 700 is then moved, e.g., pulled so the trocar engaging section 702 of the key 700 is no longer disposed in the trocar key opening 1124 of the trocar 1120.

When the key 700 is pulled, the spring 1140 spontaneously decompresses to force the spear end 1122 of the trocar 1120 out of the cannula 1110 and pierce the skin of the patient, as illustrated in FIG. 15. The sheath assembly 200 may then be positioned so the extraction post 240 of the sheath assembly 200 is coupled to the extraction opening 1125 of the trocar 1120 to capture the trocar 1120. The slidable door 1230 is then slid to the closed position, securing the sheath assembly 200 to the trocar 1120 and also enclosing the spear end 1122 of the trocar 1120 in the sheath 210 to reduce the risk of an inadvertent jab by the spear end 1122. The sheath assembly 200 may then be pulled to pull the trocar 1120 so the connected hose outflow tube is pulled through the stab wound in the skin. The trocar 1120 (and the coupled sheath assembly 200) may then be cut from the hose outflow tube. The sheath assembly 200 and the trocar 1120 may then be disposed of, in a sharps container or otherwise.

Based on the foregoing, it should be appreciated that the present invention provides a method of inserting and removing the trocar 1120. The trocar 1120 is disposed in the cannula 1110. The method includes energizing the energizer 1140 that acts on the trocar 1120, as previously described, so the energizer 1140 is able to force the trocar 1120 from the safety position where the spear end 1122 of the trocar 1120 is entirely within the cannula 1110 and the extended position where the spear end 1122 extends out of the open end 1112 of the cannula 1110. The coupled sheath 210 covers the trocar 1120 in the extended position. The trocar 1120 is held in the safety position with the key 700 that is coupled with the trocar 1120 and extends through the cannula 1110. The sheath 210 is uncoupled so the open end 1112 of the cannula 1110 is uncovered. The open end 1112 of the cannula 1110 is placed on or adjacent to the skin of the patient and the key 700 is moved to release the trocar 1120 so the energizer 1140 forces the trocar 1120 from the safety position to the extended position such that the spear end 1122 pierces the skin of the patient. The spear end 1122 of the trocar 1120 is captured using the sheath 210 by fitting the extension post 240 of the sheath 210 in the extraction opening 1125 of the trocar 1120. In some embodiments, the slidable door 1230 is moved to the closed position to close the opening 213 in the sheath 210 and enclose/conceal the spear end 1122.

From the foregoing, it should be appreciated that the trocar assembly 10 provided according to the present invention allows a trocar 1120 to be safely deployed and disposed of during use. The deployment assembly 100 may be prepared for deployment using the key 700 to displace the trocar 1120 and energize the spring 1140. Displacement of the trocar 1120 also drives the hose barb 1130 and the anchor 1126 into a hose outflow tube, allowing the deployment assembly 100 to be coupled to hose outflow tubes with varying diameters. The key 700 is pulled from the deployment assembly 100 to deploy the trocar 1120, which is less likely to accidentally occur than, for example, simply using a deployment assembly that is always free to displace the trocar. The sheath assembly 200 encloses the spear end 1122 of the trocar 1120 while the spear end 1122 extends out of the cannula 1110 prior to energizing the spring 1140, reducing the risk of an inadvertent jab by the spear end 1122. The sheath assembly 200 may also be used to bend the cannula 1110 with little risk to the user. Following creation of the stab wound by the trocar 1120 after deployment, the sheath assembly 200 can also be used to safely extract the trocar 1120 with the spear end 1122 shielded. Thus, the trocar assembly 10 provided according to the present invention can be used to safely deploy and extract a trocar 1120.

Referring now to FIGS. 16A-19, another exemplary embodiment of a trocar assembly 1600 provided according to the present invention is illustrated. Similarly to the previously described trocar assembly 10, the trocar assembly 1600 includes a deployment assembly 1610 and a sheath assembly 1620 removably coupled to the deployment assembly 1610. The deployment assembly 1610 includes a cannula 1611, a trocar 1612 disposed in the cannula 1611 and moveable between a safety position where a spear end of the trocar 1612 is entirely within the cannula 1611 and an extended position where the spear end of the trocar 1612 extends out of the cannula 1611, and an energizer 1613 acting on the trocar 1612 and configured to force the trocar 1612 from the safety position to the extended position. A key 1614 is also provided that is releasably coupled with the trocar 1612 and extends through the cannula 1611 such that the key 1614 holds the trocar 1612 in the safety position when coupled with the trocar 1612 in the safety position and uncoupling the key 1614 from the trocar 1612 allows the energizer 1613 to force the trocar 1612 from the safety position to the extended position. The sheath assembly 1620 includes a sheath 1621 that covers the open end of the cannula 1611.

Unlike the previously described deployment assembly 100, the deployment assembly 1610 of FIGS. 16A-19 includes a displacement sleeve 1630 that is displaceable along an exterior of the cannula 1611. The displacement sleeve 1630 includes a sleeve opening 1631 in which a portion of the key 1614 is disposed. The key 1614 may also have a portion that is displaceable within a cannula track 1615 formed in the cannula 1611 and a portion that engages the trocar 1612 so displacement of the key 1614 causes displacement of the trocar 1612, similar to the previously described key 700. The displacement sleeve 1630 may be displaced along the exterior of the cannula 1611 to also displace the key 1614 so the trocar 1612 displaces to the safety position, simultaneously energizing the energizer 1613. The displacement sleeve 1630 may include a pair of grasping handles 1632 that are easily gripped by a user.

Figure 16A:
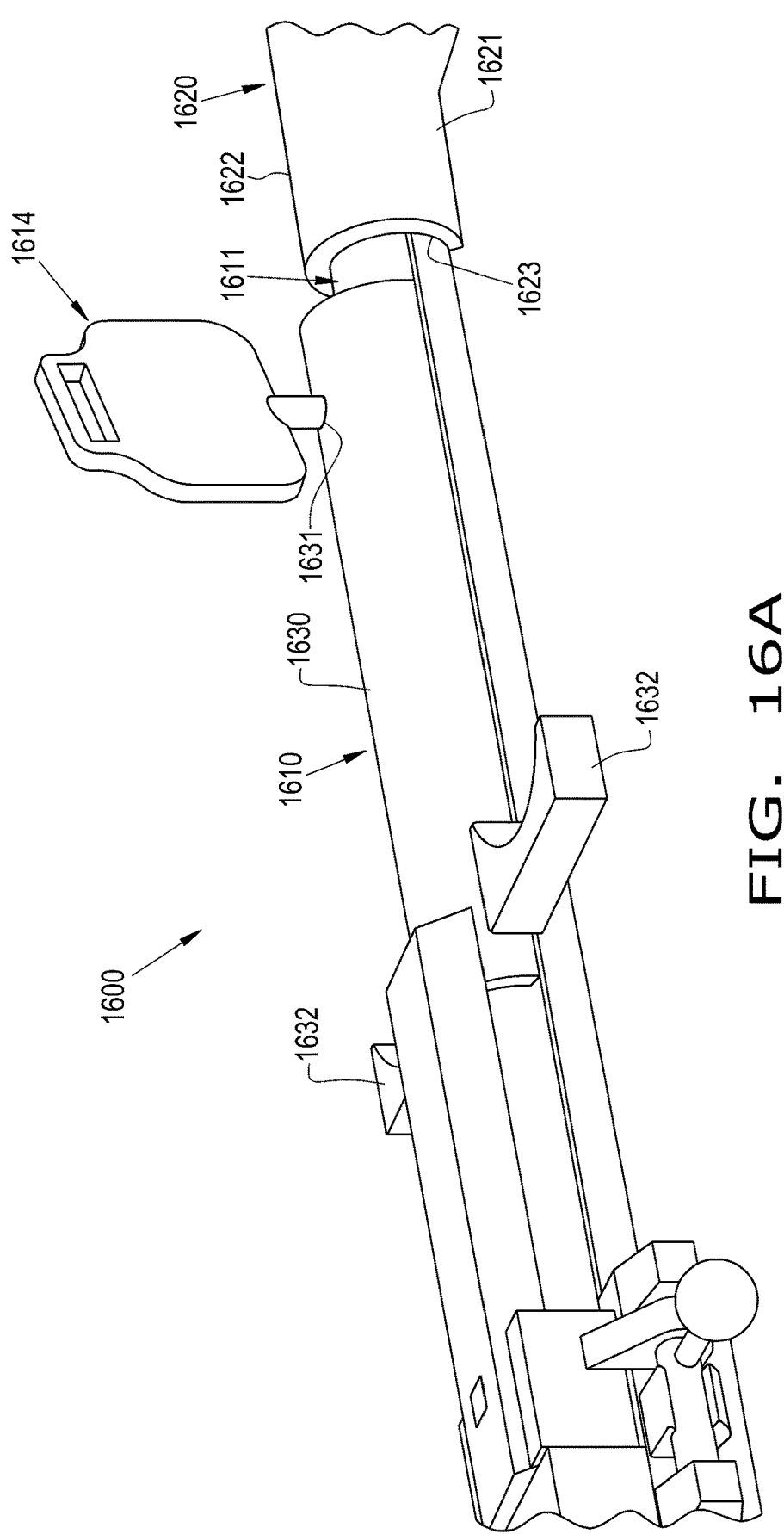
FIG. 16A is a perspective view of another exemplary embodiment of a trocar assembly provided according to the present invention with a trocar in an extended position.
Figure 16B:
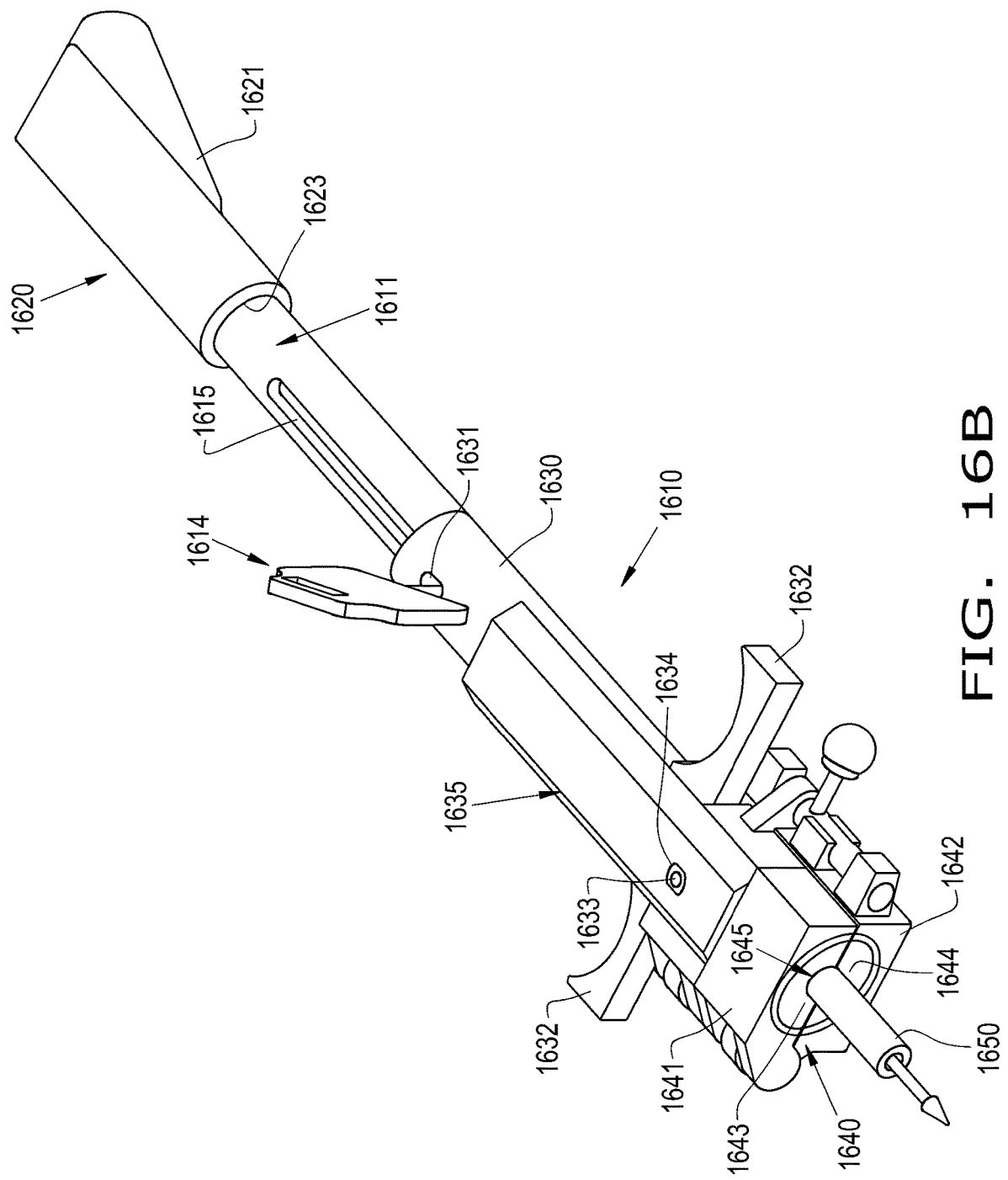
FIG. 16B is a perspective view of the trocar assembly of FIG. 16A with the trocar in a safety position.

Once the trocar 1612 is in the safety position, the key 1614 may engage a feature of the deployment assembly 1610, such as a locking opening formed in the cannula 1611, to hold the trocar 1612 in the safety position with the energizer 1613 energized. Moving the key 1614 so it uncouples from the trocar 1612 in the safety position then allows the energizer 1613 to force the trocar 1612 from the safety position to the extended position. The displacement sleeve 1630, on the other hand, may stay in place when the energizer 1613 forces the trocar 1612 to the extended position. The displacement sleeve 1630 may include a locking tab 1633 that fits inside a corresponding locking opening 1634 formed in a section 1635 that does not displace with the displacement sleeve 1630, as best illustrated in FIG. 16B. When the displacement sleeve 1630 is fully displaced so the trocar 1612 is in the safety position, the locking tab 1633 may be biased into the locking opening 1634 so the displacement sleeve 1630 is locked in place. The locking tab 1633 may, for example, be formed of a resilient material that is loaded so the locking tab 1633 spontaneously moves into the locking opening 1634 when aligned with the locking opening 1634, i.e., when the displacement sleeve 1630 is fully displaced.

The cannula 1611 may include a plurality of cannula sections, such as two cannula sections 1616A, 1616B, that are hingedly coupled to one another. The cannula sections 1616A, 1616B together define the cannula 1611. The displacement sleeve 1630 may slide along one of the cannula sections, such as the cannula section 1616B. As illustrated in FIG. 19, the cannula sections 1616A, 1616B may be unlocked from one another by moving a deadbolt 1617 from a locking position (illustrated in FIGS. 16A-18) to an unlocked position (illustrated in FIG. 19) so the deadbolt 1617 is no longer disposed in a deadbolt opening 1618 coupled to the cannula section 1616B, allowing the cannula sections 1616A, 1616B to separate. When the cannula sections 1616A, 1616B are separated, an extraction post 1619 of the cannula section 1616B may be exposed, which may then be fit into an extraction opening 1636 of the trocar 1612 to capture the trocar 1612. Once the extraction post 1619 has been fit in the extraction opening 1636 to capture the trocar 1612, the cannula sections 1616A, 1616B can be hinged back together and locked with the deadbolt 1617 to safely enclose the spear end of the trocar 1612 and remove the trocar 1612.

Figure 18:
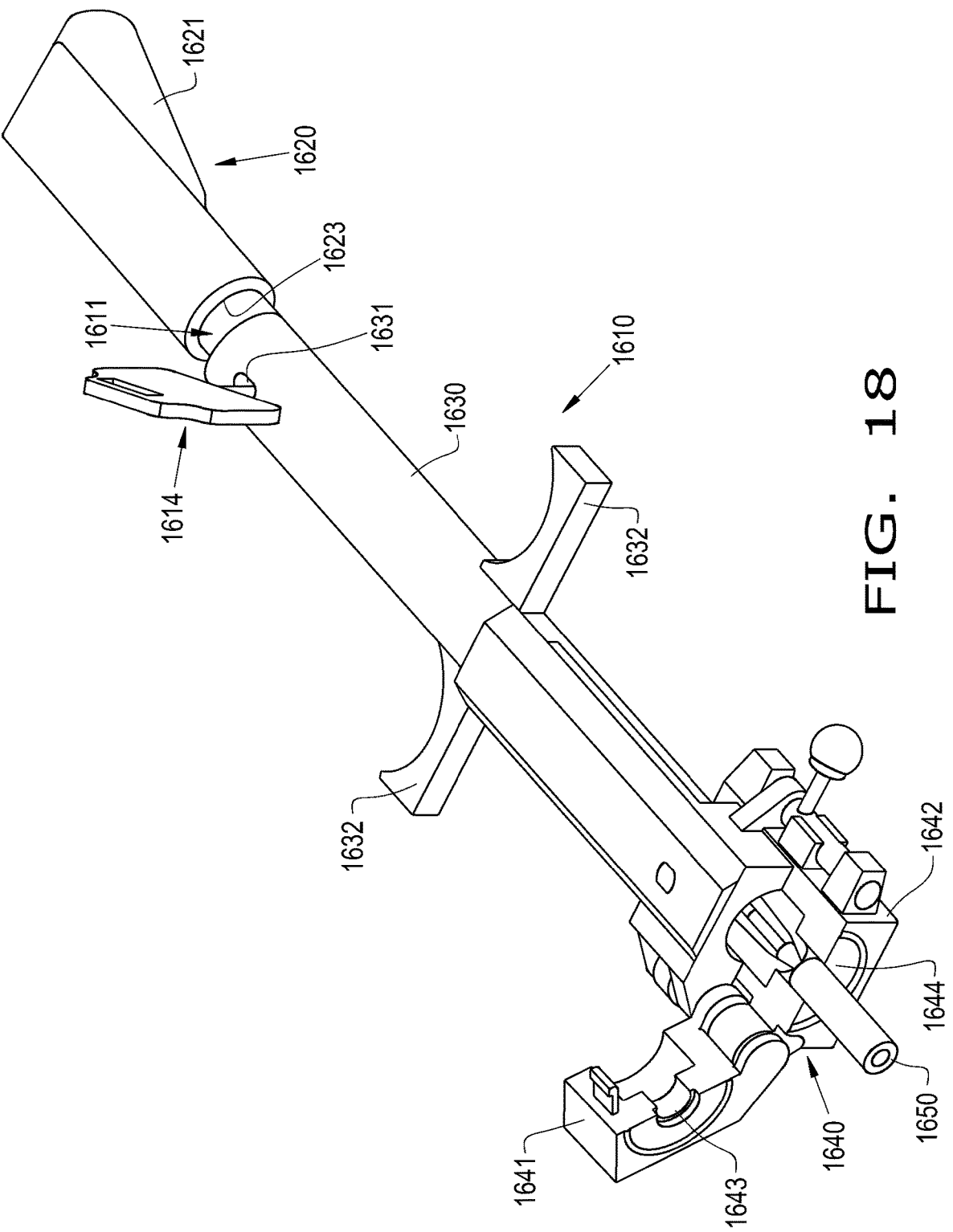
FIG. 18 is a perspective view of the trocar assembly of FIGS. 16A-16B when a hose locking section has been opened.
Figure 19:
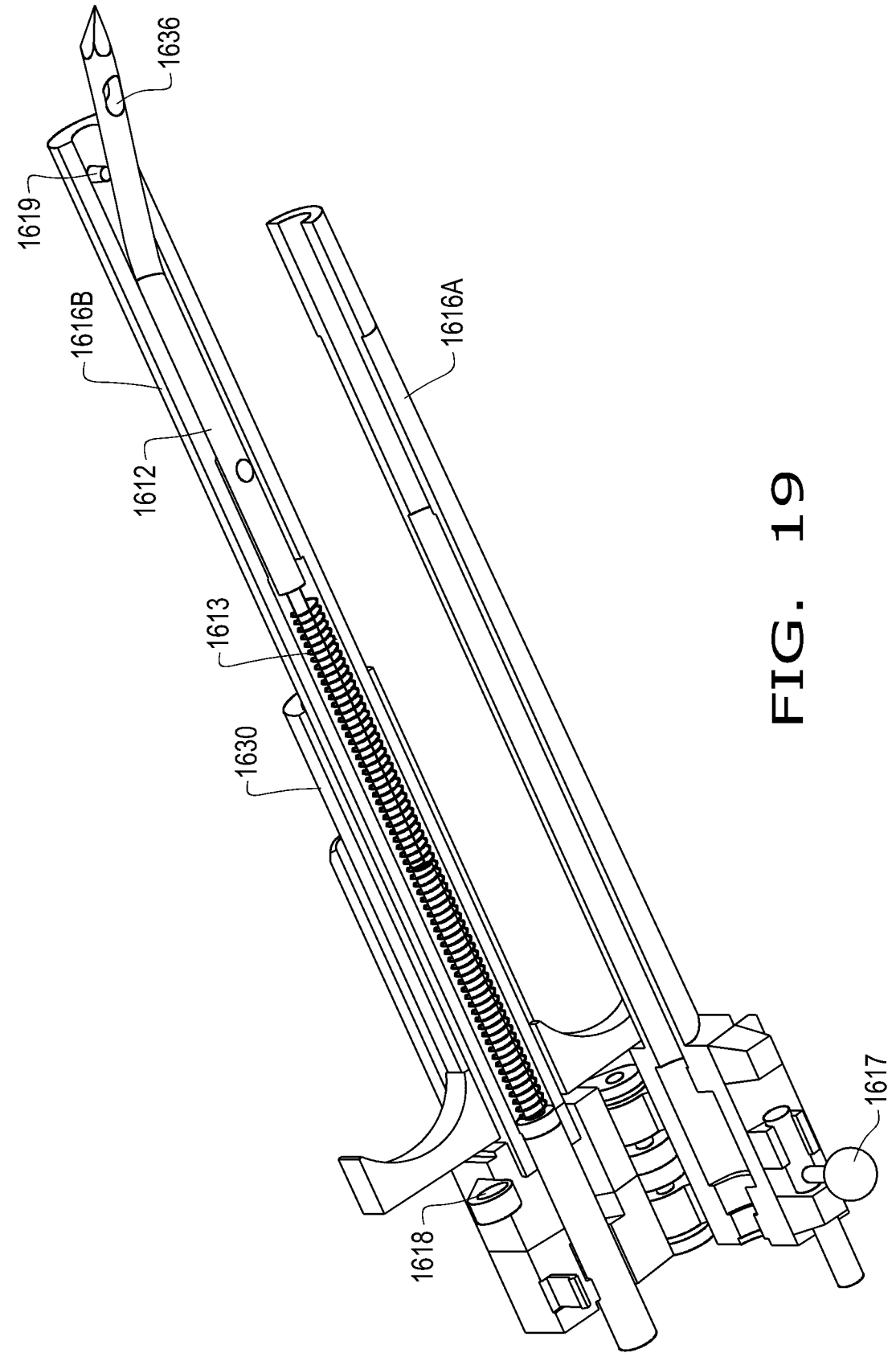
FIG. 19 is a perspective view of the trocar assembly of FIGS. 16-16B when a cannula has been opened.

Referring specifically to FIGS. 16B and 18, it is illustrated that the trocar assembly 1600 includes a hose locking section 1640 that is coupled to the cannula 1611 and includes a first lock section 1641 and a second lock section 1642. Each of the lock sections 1641, 1642 have a respective lock opening groove 1643, 1644. The first lock section 1641 is pivotable with respect to the second lock section 1642 from a closed position (illustrated in FIG. 16B) where the lock opening grooves 1643, 1644 together form a lock opening 1645 that is aligned with the trocar 1612 to an open position (illustrated in FIG. 18) where the lock opening grooves 1643, 1644 are separated. A diameter of the lock opening 1645 may be the same, or slightly smaller, than an outflow tube 1650 that is coupled to the trocar 1612 and/or the cannula 1611. When the lock sections 1641, 1642 are separated, the outflow tube 1650 can be easily aligned to the trocar 1612 and/or the cannula 1611 due to greater access of both elements. When the lock sections 1641, 1642 are closed together to form the lock opening 1645, the lock grooves 1643, 1644 may bear on the outflow tube 1650 to hold the outflow tube 1650 in place.

Figure 17:
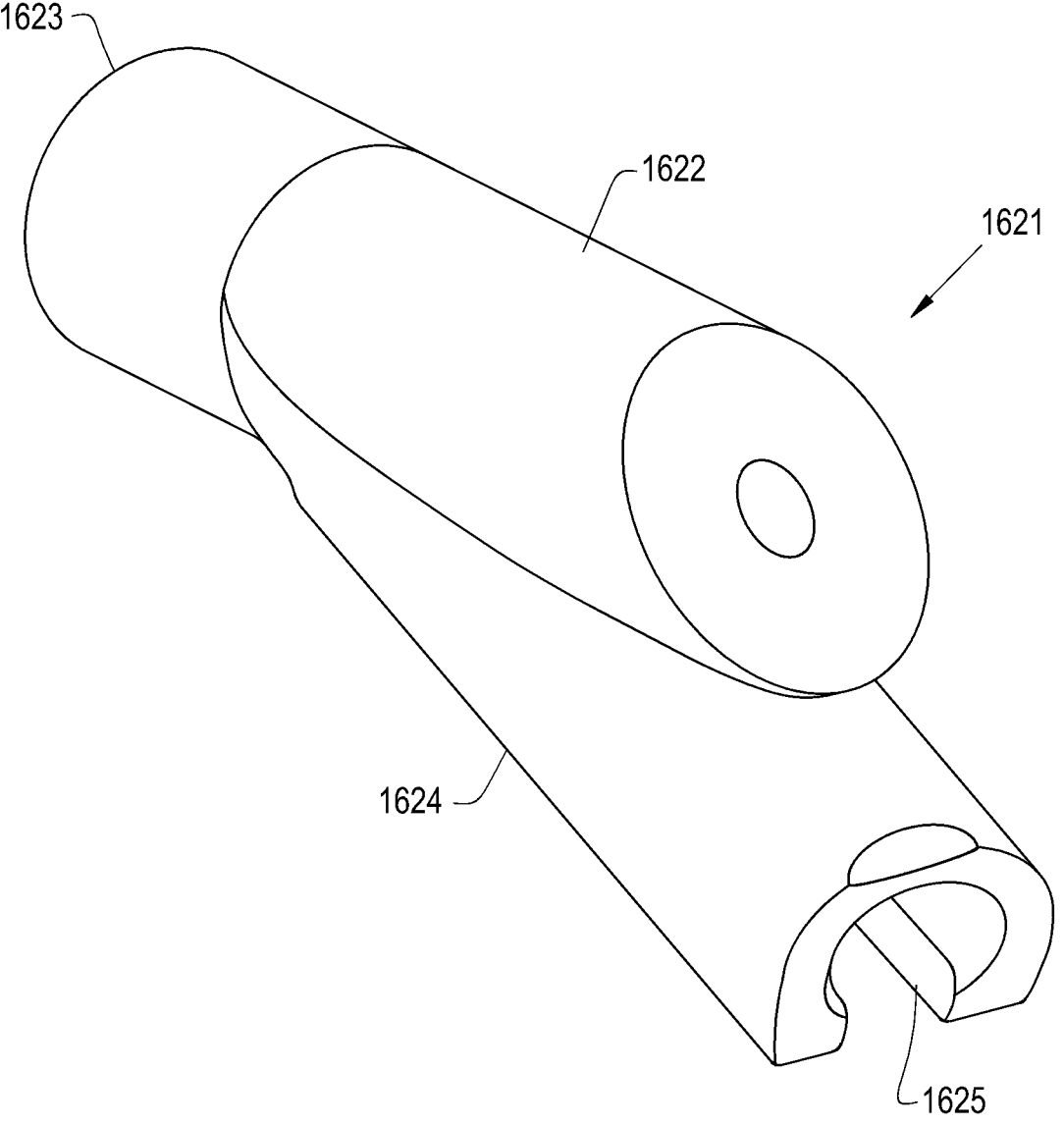
FIG. 17 is a perspective view of a sheath assembly of the trocar assembly of FIGS. 16A-16B.

Referring specifically to FIG. 17, it is illustrated that the sheath assembly 1620 includes a sheath 1621 with a first sheath section 1622 having a first sheath opening 1623 that is aligned with the cannula 1611 and a second sheath section 1624 having a second sheath opening 1625 that extends at an angle relative to the first sheath opening 1623. The trocar 1612 may be a flexible trocar that can deform, i.e., bend, during deployment. As can be appreciated from FIG. 19, the spear end of the flexible trocar 1612 may extend at an angle relative to the body of the trocar 1612. The entire trocar 1612 may be initially provided straight. The sheath assembly 1620 may be coupled to the deployment assembly 1610 initially with the trocar 1612 entirely straight and partially held in the first sheath opening 1623. The trocar 1612 may then be bent by deploying the trocar 1612. As the trocar 1612 is forced to the extended position by the energizer 1613, the trocar 1612 is redirected into the second sheath opening 1625 and is bent during the redirection. Since the first sheath opening 1623 is aligned with the body of the trocar 1612 when the trocar 1612 is straight and the second sheath opening 1625 extends at an angle relative to the first sheath opening 1623, the flexible trocar 1612 becomes bent to the angle of the second sheath opening 1625 relative to the first sheath opening 1623 when the trocar 1612 is redirected into the second sheath opening 1625. The bent trocar 1612 is further forced to the extended position where the spear end of the trocar 1612 extends out of the second sheath opening 1625 at the proper bent angle. In this respect, the sheath 1621 can provide a convenient, safe, and reliable way to conceal the sharp trocar 1612 before retracting and deploying the trocar 1612 along the proper, angled trajectory.

Figure 20:
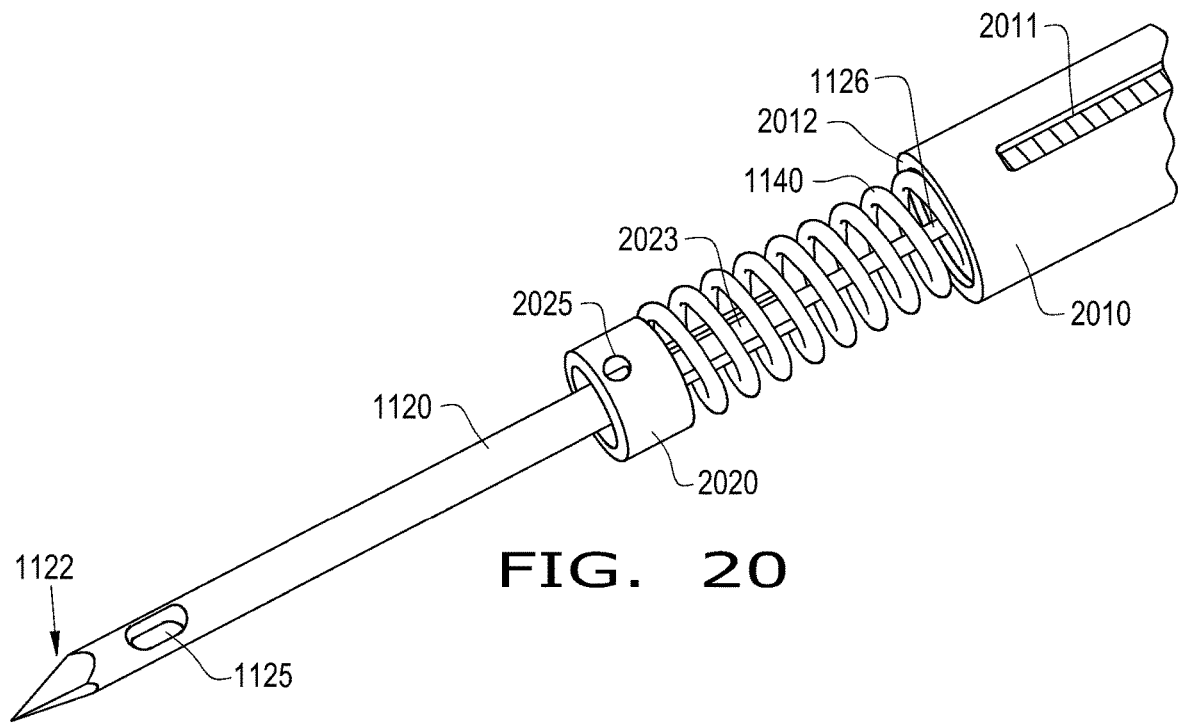
FIG. 20 is a perspective view of an exemplary embodiment of a trocar extension assembly that includes a spring sleeve and a trocar piston.
Figure 21:
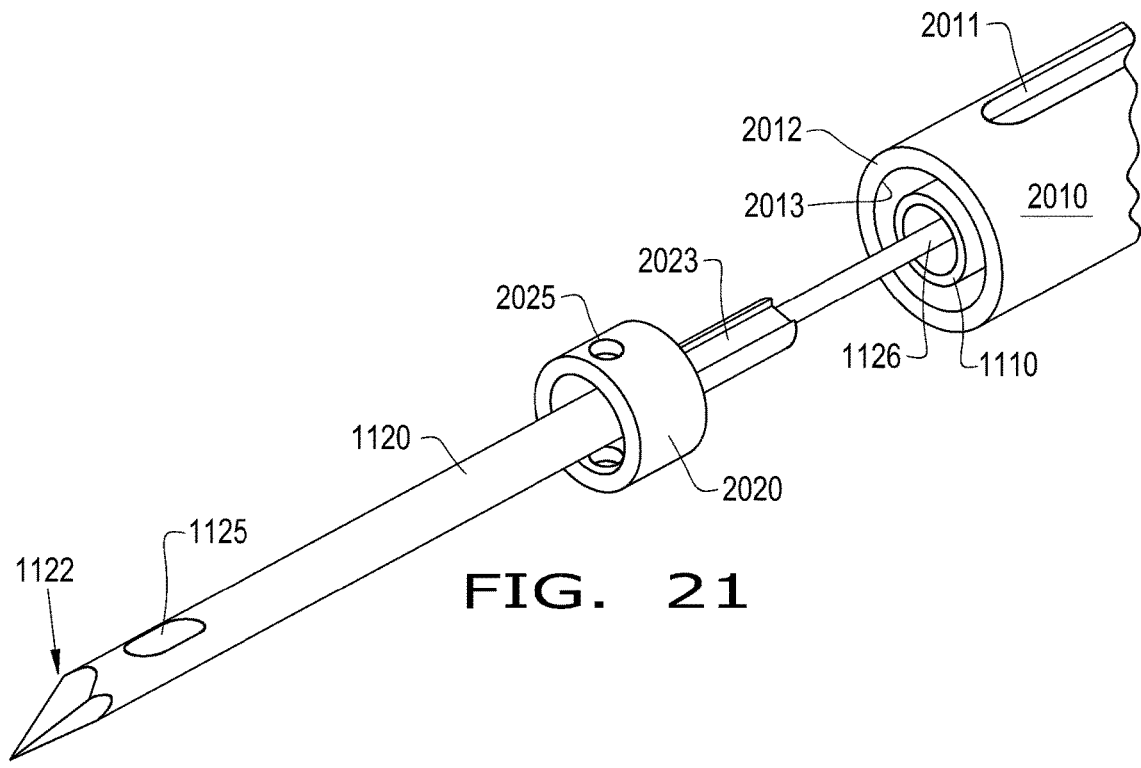
FIG. 21 is another perspective view of the portion of the trocar extension assembly of FIG. 20 with a spring removed.
Figure 22:
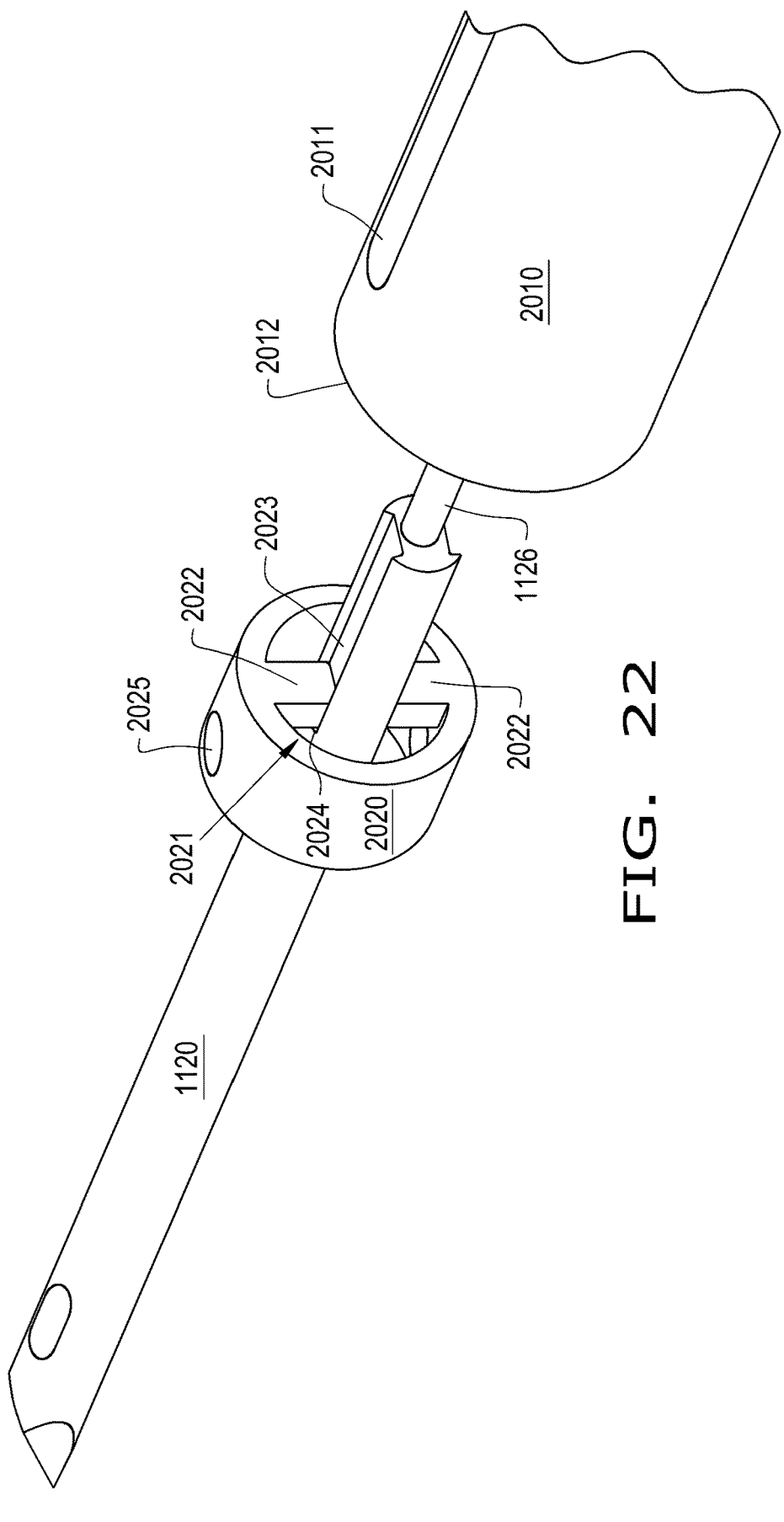
FIG. 22 is another perspective view of the portion of the trocar extension assembly of FIGS. 20-21 with the spring removed so a trocar engagement section of the trocar piston is visible.

Referring now to FIGS. 20-22, the trocar extension assembly 110 of the deployment assembly 100 is illustrated with a spring sleeve 2010 and a trocar piston 2020. The spring sleeve 2010 is disposed over the cannula 1110 and the spring 1140 is disposed between the spring sleeve 2010 and the cannula 1110. The spring sleeve 2010 has a sleeve track 2011 that aligns with the cannula track 1111 to allow the key 700 to displace within the cannula track 1111, as previously described. The trocar piston 2020 is engaged with the trocar 1120. The energizer 1140 acts on the trocar piston 2020 to force the trocar 1120 from the safety position to the extended position due to the engagement between the trocar piston 2020 and the trocar 1120. It should be appreciated that while the trocar piston 2020 is illustrated as being a ring having a circular cross-section, in some embodiments the trocar piston 2020 is provided as a partial ring with a cross-section that does not extend a full 360°, e.g., a semi-circular cross-section.

The spring sleeve 2010 has an open end 2012 that allows the trocar 1120 to move to the extended position out of the spring sleeve 2010. As best illustrated in FIG. 22, the trocar piston 2020 has a piston opening 2021 that the trocar 1120 extends through and at least one piston projection, illustrated as a pair of piston projections 2022, that extend into the piston opening 2021 and are held in respective piston grooves 2023 formed in the trocar 1120. The piston grooves 2023 may be formed in the trocar body 1121 adjacent to the trocar stem 1126 so the trocar 1120 can be pulled through the piston opening 2021 in a direction away from the open end 2012 while a closed end 2024 of each of the piston grooves 2023 abuts against the respective piston projection 2022 so displacement of the trocar piston 2020 towards the open end 2012 carries the trocar 1120 to the extended position. It should be appreciated that the trocar piston 2020 may engage the trocar 1120 in other ways, e.g., the trocar piston 2020 may additionally or alternatively engage the trocar 1120 at the junction where the trocar body 1121 and the trocar stem 1126 intersect and/or through a different slot formed in the trocar 1120, and thus the previously described engagement between the trocar piston 2020 and the trocar 1120 is exemplary only.

The trocar 1120 and the trocar piston 2020 may be independently displaceable in one direction when uncoupled. The trocar piston 2020 may include a piston key opening 2025 that aligns with the trocar key opening 1124 so portions of the key 700 are held in both the piston key opening 2025 and the trocar key opening 1124 to translate displacement of the key 700 into corresponding displacement of the trocar 1120 and the trocar piston 2020. In this respect, it may be displacement of the trocar piston 2020 that energizes the spring 1140. The open end 2012 of the spring sleeve 2010 may have an interior lip 2013 that extends radially inward and acts as a stop for the trocar piston 2020. By having such an arrangement, the risk of the spring 1140 ejecting out of the trocar extension assembly 110 is reduced due to the trocar piston 2020 holding the spring 1140 within the spiring sleeve 2010 while also allowing the spring 1140 to displace the trocar 1120. It should be appreciated that while the trocar piston 2020 is described and illustrated as being disposed in the spring sleeve 2010, in some embodiments the trocar piston 2020 is provided without a corresponding spring sleeve 2010, and vice versa with respect to the spring sleeve 2010 being provided without a corresponding trocar piston 2020.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A trocar assembly, comprising:
   a deployment assembly comprising:
      a trocar extension assembly comprising:
         a cannula comprising an open end;
         a trocar disposed in the cannula and comprising a spear end; and
         an energizer acting on the trocar and configured to force the trocar from a safety position where the spear end is entirely within the cannula to an extended position where the spear end extends out of the open end of the cannula;
      a locking assembly comprising a key releasably coupled with the trocar and extending through the cannula such that the key holds the trocar in the safety position when coupled with the trocar in the safety position and uncoupling the key from the trocar allows the energizer to force the trocar from the safety position to the extended position; and
      a sheath assembly removably coupled to the deployment assembly, the sheath assembly comprising a sheath that covers the open end of the cannula, wherein the trocar comprises an extraction opening and the sheath comprises an extraction post that is shaped and sized to fit within the extraction opening of the trocar to capture the trocar.

2. The trocar assembly of claim 1, wherein the cannula comprises a cannula track and a portion of the key is disposed in the cannula track, the key being displaceable within the cannula track in a displacement direction to displace the trocar within the cannula when the key is coupled to the trocar.

3. The trocar assembly of claim 2, wherein displacement of the trocar away from the open end of the cannula by displacing the key in the displacement direction within the cannula track energizes the energizer.

4. The trocar assembly of claim 2, wherein the key is displaceable within the cannula track to displace the trocar from the extended position to the safety position when the key is coupled to the trocar.

5. The trocar assembly of claim 2, wherein the locking assembly comprises an insert comprising insert teeth and a gear comprising gear teeth intermeshed with the insert teeth and a gear opening, the key comprising a gear engaging section fit within the gear opening such that rotation of the key causes a corresponding rotation of the gear and displacement of the key within the cannula track.

6. The trocar assembly of claim 2, further comprising a locking system configured to prevent the key from displacing in an opposite direction to the displacement direction.

7. The trocar assembly of claim 2, further comprising a displacement sleeve that is displaceable along an exterior of the cannula and comprises a sleeve opening in which a portion of the key is disposed.

8. The trocar assembly of claim 1, further comprising a housing in which the trocar extension assembly is disposed, the housing comprising a track that accepts the key.

9. The trocar assembly of claim 8, further comprising a hose barb that is housed in the housing and is configured to couple to a hose outflow tube, the hose barb comprising a barbed end, an end opposite the barbed end, and a through-opening extending through the barbed end and the opposite end of the hose barb, the trocar comprising an anchor opposite the spear end and a stem coupled to the anchor, a portion of the stem and the anchor extending out of the barbed end when the trocar is in the safety position.

10. The trocar assembly of claim 1, wherein the sheath assembly comprises a slidable door that is slidably coupled to the sheath, the door being slidable between an open position and a closed position to respectively uncover or cover an opening formed in the sheath.

11. The trocar assembly of claim 10, wherein the extraction post is uncovered when the door is in the open position and is covered when the door is in the closed position.

12. The trocar assembly of claim 1, wherein the sheath covers the spear end of the trocar in the extended position when the sheath assembly is coupled to the deployment assembly.

13. The trocar assembly of claim 1, wherein the sheath assembly comprises an arced cannula bender extending between two side walls of the sheath, the cannula bender being configured to bend the cannula when the sheath assembly is partially uncoupled from the deployment assembly.

14. The trocar assembly of claim 1, wherein the energizer comprises a spring bearing on the trocar.

15. The trocar assembly of claim 1, wherein the cannula comprises a plurality of cannula sections hinged to one another, the cannula sections together defining the cannula.

16. The trocar assembly of claim 1, further comprising a hose locking section that is coupled to the cannula and comprises a first lock section and a second lock section, each of the first lock section and the second lock section comprising a respective lock opening groove, the first lock section being pivotable relative to the second lock section from a closed position where the respective lock opening grooves together form a lock opening that is aligned with the trocar to an open position where the respective lock opening grooves are separated.

17. The trocar assembly of claim 1, wherein the sheath comprises a first sheath section comprising a first sheath opening that is aligned with the cannula and a second sheath section comprising a second sheath opening that extends at an angle relative to the first sheath opening.

18. The trocar assembly of claim 1, further comprising a trocar piston engaged with the trocar, the energizer acting on the trocar piston to force the trocar from the safety position to the extended position.

19. A method of inserting and removing a trocar, the trocar being disposed within a cannula, the method comprising:
   energizing an energizer that acts on the trocar, the energizer being configured to force the trocar from a safety position where a spear end of the trocar is entirely within the cannula and an extended position where the spear end extends out of an open end of the cannula, wherein a coupled sheath covers the open end of the cannula;
   holding the trocar in the safety position with a key that is coupled with the trocar and extends through the cannula;
   uncoupling the sheath so the open end of the cannula is uncovered;

placing the open end of the cannula on or adjacent to the skin of a patient;

moving the key to release the trocar so the energizer forces the trocar from the safety position to the extended position such that the spear end pierces the skin of the patient; and capturing the spear end of the trocar using the sheath by fitting an extension post of the sheath in an extraction opening formed in the trocar.

20. A trocar assembly, comprising:

a deployment assembly comprising:

a trocar extension assembly comprising:

a cannula comprising an open end;

a trocar disposed in the cannula and comprising a spear end; and an energizer acting on the trocar and configured to force the trocar from a safety position where the spear end is entirely within the cannula to an extended position where the spear end extends out of the open end of the cannula;

a locking assembly comprising a key releasably coupled with the trocar and extending through the cannula such that the key holds the trocar in the safety position when coupled with the trocar in the safety position and uncoupling the key from the trocar allows the energizer to force the trocar from the safety position to the extended position;

a sheath assembly removably coupled to the deployment assembly, the sheath assembly comprising a sheath that covers the open end of the cannula; and a hose locking section that is coupled to the cannula and comprises a first lock section and a second lock section, each of the first lock section and the second lock section comprising a respective lock opening groove, the first lock section being pivotable relative to the second lock section from a closed position where the respective lock opening grooves together form a lock opening that is aligned with the trocar to an open position where the respective lock opening grooves are separated.

21. A trocar assembly, comprising:

a deployment assembly comprising:

a trocar extension assembly comprising:

a cannula comprising an open end;

a trocar disposed in the cannula and comprising a spear end; and an energizer acting on the trocar and configured to force the trocar from a safety position where the spear end is entirely within the cannula to an extended position where the spear end extends out of the open end of the cannula;

a locking assembly comprising a key releasably coupled with the trocar and extending through the cannula such that the key holds the trocar in the safety position when coupled with the trocar in the safety position and uncoupling the key from the trocar allows the energizer to force the trocar from the safety position to the extended position; and a sheath assembly removably coupled to the deployment assembly, the sheath assembly comprising a sheath that covers the open end of the cannula, the sheath comprising a first sheath section comprising a first sheath opening that is aligned with the cannula and a second sheath section comprising a second sheath opening that extends at an angle relative to the first sheath opening.

\* \* \* \* \*